US012622863B2

(12) United States Patent (10) Patent No.: US 12,622,863 B2
Panzieri et al. (45) Date of Patent: May 12, 2026

(54) INJECTABLE COMPOSITION AND USE OF SAID COMPOSITION

(71) Applicant: INNATE S.R.L., Novi Ligure (IT)

(72) Inventors: Federico Panzieri, Novi Ligure (IT); Giulia Avio, Novi Ligure (IT); Cosimo Celino, Novi Ligure (IT)

(73) Assignee: INNATE S.R.L., Novi Ligure (IT)

( * ) Notice: Subject to any disclaimer, the term of this patent is extended or adjusted under 35 U.S.C. 154(b) by 390 days.

(21) Appl. No.: 18/033,866

(22) PCT Filed: Oct. 25, 2021

(86) PCT No.: PCT/IB2021/059825

§ 371 (c)(1),
(2) Date: Apr. 26, 2023

(87) PCT Pub. No.: WO2022/090897

PCT Pub. Date: May 5, 2022

(65) Prior Publication Data

US 2023/0398053 A1 Dec. 14, 2023

(30) Foreign Application Priority Data

Oct. 26, 2020 (IT) ........................ 102020000025264

(51) Int. Cl.

| | |
|---|---|
| *A61K 8/73* | (2006.01) |
| *A61K 8/04* | (2006.01) |
| *A61K 8/67* | (2006.01) |
| *A61L 27/20* | (2006.01) |
| *A61L 27/50* | (2006.01) |
| *A61L 27/52* | (2006.01) |
| *A61Q 19/08* | (2006.01) |

(52) U.S. Cl.
CPC .............. *A61K 8/735* (2013.01); *A61K 8/042* (2013.01); *A61K 8/675* (2013.01); *A61L 27/20* (2013.01); *A61L 27/505* (2013.01); *A61L 27/52* (2013.01); *A61Q 19/08* (2013.01); *A61K 2800/91* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 2007/0196421 A1* | 8/2007 | Hunter ................. | A61K 31/496 623/23.72 |
| 2011/0104225 A1* | 5/2011 | Rochkind ............... | A61P 43/00 435/395 |

FOREIGN PATENT DOCUMENTS

| | | | | |
|---|---|---|---|---|
| CN | 108578784 A | * | 9/2018 | ......... A61L 27/3839 |
| KR | 101984688 B1 | * | 5/2019 | .......... B29C 64/106 |
| WO | 2012062775 A1 | | 5/2012 | |
| WO | 2020104915 A1 | | 5/2020 | |

OTHER PUBLICATIONS

International Search Report, PCT/IB2021/059825, Feb. 10, 2022 (9 Pages).

* cited by examiner

*Primary Examiner* — Dale R Miller
(74) *Attorney, Agent, or Firm* — Falcon Rappaport & Berkman LLP

(57) ABSTRACT

Injectable composition in hydrogel form, comprising water, hyaluronic acid, and nicotinamide for inhibiting the action of the hyaluronidase in the injected condition of the composition.

7 Claims, No Drawings

INJECTABLE COMPOSITION AND USE OF SAID COMPOSITION

The present invention relates to an injectable composition in hydrogel form, comprising water and hyaluronic acid.

Hyaluronic acid is a very biocompatible natural polysaccharide, present in all human tissues, and is one of the fundamental components of connective tissues. It is distributed ubiquitously in animal tissues and fluids, in high concentrations in synovial fluids, in the vitreous humour and in the skin, and is mainly responsible for the viscosity and lubricating activity of synovial fluid. In cartilage, hyaluronic acid acts as a support for the aggregation of proteoglycans and proteins.

Hyaluronic acid is a long glycosaminoglycan composed of repeated disaccharides of glucuronic acid and N-acetyl-glucosamine with high molecular weight and high viscosity.

Hyaluronic acid is currently prepared as a gel from a powder in which it is present as a salt (sodium hyaluronate), and in such a gel it forms water micelles thanks to its high affinity with water itself. A crystalline gel is then formed which, when injected, achieves prolonged durability in tissues, as it maintains biocompatibility.

Hyaluronic acid is used for example in aesthetic medicine to increase the volume of facial tissues, to correct wrinkles, skin folds, to increase the volume of the lips, and in general to correct skin imperfections. In this case it can be injected inside a scar or at the level of the superficial dermal layer for skin treatments and act as a skin moisturiser or even as a filler and therefore anti-wrinkle substance. This action is made possible thanks to the viscoelastic and hydrating properties of hyaluronic acid, which is naturally present in the extracellular matrix of skin with the function of regulating hydration and elasticity. The intradermal administration of the aid allows to give tissues a good amount of hyaluronic acid to counteract the skin aging process.

Alternatively, hyaluronic acid is used for intra-articular administration, in the treatment of osteoarthritis, for example in the knee, where it is naturally found in the synovial fluid, of which it is the main substance responsible for the high lubricating capacities thanks to the viscosity thereof. Hyaluronic acid contributes to lubricating the joint and cushioning mechanical stresses, and therefore has a lubricating function and a cushioning function. It also protects the cartilage from the penetration of inflammatory cells and from the lithic enzymes which degrade it.

In intra-articular infiltrations, the preparation generally consists of a sodium salt of a high molecular weight and high purity fraction of hyaluronic acid. The short half-life of this molecule at the joint level means that its effectiveness is not simply linked to the restoration of physiological levels of hyaluronic acid in osteoarthritic joints. The evaluations carried out in patients with osteoarthritis and other arthropathies involving the knee have shown an action which, in principle, exerts an anti-inflammatory activity of the molecule.

Microarthroscopy studies and ultrastructural studies on the joint cartilage and synovial membrane have also shown that there is a possible repair of degenerative joint lesions in humans following intra-articular use of the drug.

Compositions of this type must address the degradation of the hyaluronic acid over time; in fact, this degradation affects the so-called shelf life, i.e., the duration of the period from production to sale in which the total quality of the product must be maintained intact, and above all the duration of the effect on the body following administration.

The duration of hyaluronic acid strongly depends on the type of treatment to which it is subjected and its composition. Two categories can be distinguished: linear hyaluronic acid and cross-linked (or reticulated) hyaluronic acid. Special cross-linking agents such as BDDE (1,4 butanediol diglidyl ether) or DVS (Divinyl Sulfone) are used to switch from linear to cross-linked hyaluronic acid.

Currently the compositions exhibiting the longest durability are those comprising cross-linked hyaluronic acid. However, the presence of traces of BDDE or other cross-linking agents at the end of the cross-linking reaction is problematic in several respects, for example because in the immediate term it may trigger intracutaneous reactivity actions and in the long term it may cause the onset of subcutaneous granulomas.

A major cause of the degradation of hyaluronic acid is the action of the enzyme hyaluronidase. This enzyme acts very effectively on linear hyaluronic acid, while the three-dimensional structure of the cross-linked hyaluronic acid assumed by virtue of the cross-linking process makes the action of the enzyme difficult.

Therefore, in the state of the art, the request for a longer duration of the composition requires the use of cross-linked hyaluronic acid, to the detriment of an increase in risks to the user's health and safety.

The use of antioxidants and stabilizers, which act as protectors of the biomolecules against environmental stresses, such as high temperatures, is known to ensure a greater durability of hyaluronic acid.

There is therefore an unmet need in the state of the art for a composition in the hydrogel form comprising hyaluronic acid which ensures a longer duration and lower risks for the patient.

The present invention meets this technical need and overcomes the limits set forth above related to the compositions currently known in the state of the art and aims to constitute a functional and advantageous solution both as an embodiment and as a use.

These objects are obtained, according to the invention, by providing an injectable composition in the form of a hydrogel, comprising water, hyaluronic acid and nicotinamide (or niacinamide or vitamin B3) for inhibiting the action of the hyaluronidase in the injected condition of the composition.

In an exemplary embodiment, said hyaluronic acid is linear.

In a further exemplary embodiment, said hyaluronic acid comprises between 1000 KDa to 4000 KDa of high molecular weight sodium hyaluronate, preferably between 1500 KDa and 3000 KDa.

The use of linear hyaluronic acid allows to avoid the problems for the patient's health which are instead exhibited by cross-linked hyaluronic acid.

From this point of view, the presence of nicotinamide in the composition becomes crucial, to counterbalance the shorter duration of the linear hyaluronic acid with respect to cross-linked hyaluronic acid.

In fact, the Applicant has demonstrated that, surprisingly, nicotinamide has an inhibitory effect on hyaluronidase, consequently acting as a protector of hyaluronic acid.

Nicotinamide is the precursor of important NAD cofactors and their phosphoric derivatives (NADP); according to the state of the art, this is commonly considered a valid agent in the treatment of inflammatory skin diseases caused by the formation of antibodies, and it is known to perform an antioxidant action being an important component of coenzymes which participate in the transport of oxygen. It is also known to have a negative effect on sebum production, increase keratin synthesis and accelerate the differentiation of keratinocytes with improvement of dermo-epidermal function. Lastly, it is used in widespread diseases such as acne, seborrhoeic dermatitis, atopic and contact dermatitis, rosacea, hyper-pigmentation and in anti-aging formulations.

To the best of the Applicant's knowledge, there is no state of the art study which describes or anticipates the inhibitory effect on hyaluronidase by nicotinamide.

Cross-linked hyaluronic acid has an altered three-dimensional shape which makes it hard to be attacked by the action of hyaluronidase, while this does not occur for linear hyaluronic acid. Therefore, the present invention arises from the surprising observation that linear hyaluronic acid can be protected from nicotinamide by masking the action sites of the hyaluronidase on the hyaluronic acid by the nicotinamide itself.

Furthermore, nicotinamide does not cause intracutaneous toxicity problems, while cross-linked hyaluronic acid does.

Therefore, the composition object of the present invention is a valid and safer substitute for the currently known long-life cross-linked hyaluronic acid products.

According to a further exemplary embodiment, the hyaluronic acid is provided in weight percentages between 1.0% and 3.0%.

According to a refinement, said hyaluronic acid consists of said sodium hyaluronate, exclusively of high molecular weight.

In a further exemplary embodiment, the nicotinamide is provided in weight percentages between 0.2% and 5.0%, preferably between 0.6% and 2.0%.

In the composition, the nicotinamide is not only a functional excipient adapted to protect the hyaluronic acid by virtue of its antioxidant action, but also acts against the action of the hyaluronidase, allowing the viscosupplementation features to be maintained over time. Experimental tests have shown that in a composition without nicotinamide, the hyaluronic acid is degraded by a 50% standard hyaluronidase after one hour; on the contrary, with a presence of nicotinamide in the percentages described above, the hyaluronic acid degrades by only 20% after one hour, while the normal products on the market degrade by 70%.

By virtue of this protection of the hyaluronic acid over time, the finished product thus acquires greater stability and greater durability over time.

The composition is particularly advantageous since by its nature, high molecular weight linear hyaluronic acid is more durable, but it is also degraded like the others; therefore, the protective action of the nicotinamide plays an important role in prolonging its effects over time.

Experimental tests have also shown that, by virtue of the action of the nicotinamide, the viscosity of the hydrogel decreases by only about 5% after almost 2 years.

The nicotinamide also acts to protect the hyaluronic acid during sterilisation and, once the product is administered, exerts an important anti-inflammatory adjuvant activity in the patient. In vitro tests have shown that the composition has a marked anti-inflammatory effect.

The composition can further advantageously comprise excipients to ensure the stability and functionality thereof.

In an embodiment, sodium chloride is comprised. This allows to adjust the osmolarity of the composition.

In a further embodiment, a buffer system is comprised. Such a buffer system can be of any suitable type.

Preferably the buffer system comprises sodium phosphate dibasic and sodium phosphate monobasic.

The buffer system can alternatively be composed of other salts, e.g., potassium equivalents, i.e., potassium phosphate dibasic and potassium phosphate monobasic.

In a further variant, the buffer system can be a citrate buffer, comprising citric acid and sodium citrate.

The buffer can be provided in all the hydration forms thereof.

According to an embodiment, said sodium phosphate dibasic is in the anhydrous and/or dihydrate and/or dodecahydrate hydration state and said sodium phosphate monobasic is in the anhydrous and/or dihydrate hydration state.

Similarly, such hydration states can be provided in the above-mentioned cases of a buffer system comprising potassium salts or a citrate buffer system.

Amino acids can also be provided in the composition.

In this case, the nicotinamide also acts to protect any amino acids added to the product.

Advantageously, the composition has the appearance of a transparent gel, an important condition for the visual control of syringes.

In an embodiment, the composition is adapted to be used in an intra-articular injection in a joint to increase the lubricating capacities of the synovial fluid of the joint.

In a further embodiment, the composition is adapted to be used in an intradermal injection for the correction of skin imperfections.

In a further embodiment, the composition is adapted to be used in a PRP administration.

Platelet-rich plasma is a known technique used to stimulate and accelerate the healing of bones and soft tissues. This technique uses an autologous plasma volume which has a platelet concentration above the base value. The normal number of platelets in the blood ranges from 150,000/μl to 350,000/μl, with an average of about 200,000/μl. The useful concentration for the regenerative effect on bones and soft tissues is generally recognised as 1,000,000/μl of platelets, typically used in a volume of 5 ml of plasma. PRP is usually injected with hyaluronic acid, which exerts a viscosupplementation necessary for successful administration. The composition of the present invention has proved particularly advantageous in this type of application.

An object of the present invention is also the use of the composition described above in an intra-articular injection to increase the lubricating capacities of the synovial fluid of joints.

An object of the present invention is also the use of the composition described above in an intradermal injection to correct skin imperfections. The composition has a moisturising effect on the skin and adds firmness, as it acts inside the layers of the dermis, increasing volume and obtaining a corrective effect of skin imperfections.

An object of the present invention is further the use of the composition described above in a PRP administration.

These and other features of the invention and the advantages resulting therefrom will become apparent from the following detailed description of an embodiment, preferred among the advantageous and various embodiments of the invention, illustrated merely by way of example, therefore non-limiting, with reference to the table below.

| Component | Weight percentage |
| --- | --- |
| Water for injections as needed to | 100 |
| Nicotinamide | 0.800 |

-continued

| Component | Weight percentage |
|---|---|
| High molecular weight sodium hyaluronate | 2.000 |
| Sodium Chloride | 0.700 |
| Sodium Phosphate Dibasic | 0.150 |
| Sodium Phosphate Monobasic | 0.030 |

In this embodiment, the sodium hyaluronate consists exclusively of high molecular weight sodium hyaluronate.

The above composition has the following physical, microbiological and chemical features:

pH: 6.50-7.50 osmolality: 270-400 mOsm/Kg density: 1,000-1,015 g/cm3 appearance: transparent gel viscosity: at least 70000 cP titre: maximum concentration of 25 mg/ml (this concentration must be suitable for both intradermal and intra-articular uses).

Sterile

Endotoxins <5 EU/mL

From the foregoing, it is therefore evident that the invention is not limited to the embodiments just described and illustrated by way of non-limiting examples, but may be varied and modified, as a whole and in individual details, especially constructively, according to the specific needs and conveniences of production and use, within the scope of the technical and functional equivalents, without abandoning the guiding principle set forth above and subsequently claimed.

The invention claimed is:

1. An injectable composition in hydrogel form, comprising water and hyaluronic acid, and further comprising nicotinamide for inhibiting action of hyaluronidase in the injected condition of the composition; wherein said hyaluronic acid is of the linear type and comprises between 1000 KDa and 4000 KDa high molecular weight sodium hyaluronate; wherein the hyaluronic acid is provided in weight percentages between 1.0% and 3.0% and the nicotinamide is provided in weight percentages between 0.2% and 5.0%.

2. The composition according to claim 1, further comprising sodium chloride.

3. The composition according to claim 1, further comprising buffer system comprising sodium phosphate dibasic and sodium phosphate monobasic.

4. The composition according to claim 3, wherein said sodium phosphate dibasic is in an anhydrous and/or dihydrate and/or dodecahydrate hydration state and said sodium phosphate monobasic is in an anhydrous and/or dihydrate hydration state.

5. A method for therapeutic treatment, in a subject in need thereof, the method comprising an intra-articular injection of the composition according to claim 1, in a joint to increase lubricating capacities of synovial fluid of the joint.

6. A method for therapeutic treatment, in a subject in need thereof, the method comprising an intradermal injection of the composition according to claim 1, to correct skin imperfections.

7. A method for therapeutic treatment, in a subject in need thereof, the method comprising administration of a composition according to claim 1, in combination with platelet-rich plasma (PRP).

\* \* \* \* \*